US009492173B2

(12) United States Patent
McWeeney et al.

(10) Patent No.: US 9,492,173 B2
(45) Date of Patent: Nov. 15, 2016

(54) METHODS AND APPARATUS FOR MAGNET-INDUCED COMPRESSION ANASTOMOSIS BETWEEN ADJACENT ORGANS

(71) Applicant: GI Windows, Inc., West Bridgewater, MA (US)

(72) Inventors: John McWeeney, Brighton, MA (US); Marvin Ryou, Melrose, MA (US); Padraig Cantillon-Murphy, Danvers, MA (US); Jeffrey H. Lang, Danvers, MA (US); Christopher Thompson, Needham, MA (US)

(73) Assignee: GI Windows, Inc., West Bridgewater, MA (US)

( * ) Notice: Subject to any disclaimer, the term of this patent is extended or adjusted under 35 U.S.C. 154(b) by 0 days.

(21) Appl. No.: 14/449,414

(22) Filed: Aug. 1, 2014

(65) Prior Publication Data
US 2014/0343583 A1    Nov. 20, 2014

Related U.S. Application Data

(63) Continuation of application No. 12/984,803, filed on Jan. 5, 2011, now Pat. No. 8,828,032.

(60) Provisional application No. 61/292,313, filed on Jan. 5, 2010.

(51) Int. Cl.
*A61B 17/08* (2006.01)
*A61B 17/11* (2006.01)
*A61B 17/00* (2006.01)

(52) U.S. Cl.
CPC .. *A61B 17/1114* (2013.01); *A61B 2017/00818* (2013.01); *A61B 2017/00876* (2013.01); *A61B 2017/1117* (2013.01); *A61B 2017/1139* (2013.01)

(58) Field of Classification Search
CPC .............................................. A61B 2017/1139
See application file for complete search history.

(56) References Cited

U.S. PATENT DOCUMENTS

| 4,538,130 A | 8/1985 | Gluckstern et al. |
| 5,300,910 A | 4/1994 | Unkelbach et al. |

(Continued)

FOREIGN PATENT DOCUMENTS

| RU | 2 018 266 C1 | 8/1994 |
| SU | 1708313 A1 | 1/1992 |
| SU | 1 725 851 A1 | 4/1992 |

OTHER PUBLICATIONS

International Search Report for PCT/US2013/041641 dated Oct. 18, 2013, 4 pages.

(Continued)

*Primary Examiner* — Gregory Anderson
(74) *Attorney, Agent, or Firm* — Brown Rudnick LLP; Mark S. Leonardo

(57) ABSTRACT

Methods and apparatus for creating an anastomosis or fistula between the gallbladder and an adjacent organ are disclosed. First, a parent magnet, typically a permanent magnet, is deployed in the stomach, small intestine, or another organ adjacent to the gallbladder, and a mating daughter material is deployed in the gallbladder in order to create a magnet-compression anastomosis. The gallbladder may then be ablated or otherwise functionally inactivated through the anastomosis. Another aspect of the invention relates to an all-in-one surgical kit that contains all the necessary specialized tools for a surgeon to perform the procedure.

20 Claims, 7 Drawing Sheets

(56) References Cited

U.S. PATENT DOCUMENTS

| | | |
|---|---|---|
| 5,595,562 A | 1/1997 | Grier |
| 6,129,668 A | 10/2000 | Haynor et al. |
| 6,352,543 B1 | 3/2002 | Cole |
| 6,652,540 B1 | 11/2003 | Cole et al. |
| 6,719,768 B1 | 4/2004 | Cole et al. |
| 6,932,827 B2 | 8/2005 | Cole |
| 7,760,059 B2 | 7/2010 | Higuchi |
| 8,118,821 B2 | 2/2012 | Mouw |
| 8,142,454 B2 | 3/2012 | Harrison et al. |
| 8,262,680 B2 | 9/2012 | Swain et al. |
| 8,439,915 B2 | 5/2013 | Harrison et al. |
| 8,623,036 B2 | 1/2014 | Harrison et al. |
| 8,864,781 B2 | 10/2014 | Surti et al. |
| 2002/0143347 A1 | 10/2002 | Cole et al. |
| 2008/0051626 A1 | 2/2008 | Sato et al. |
| 2008/0200934 A1 | 8/2008 | Fox |
| 2008/0262523 A1 | 10/2008 | Makower et al. |
| 2009/0125042 A1 | 5/2009 | Mouw |
| 2010/0099947 A1 | 4/2010 | Sato et al. |
| 2011/0144560 A1 | 6/2011 | Gagner et al. |
| 2011/0295285 A1 | 12/2011 | McWeeney et al. |
| 2012/0197062 A1 | 8/2012 | Requarth |
| 2012/0259350 A1 | 10/2012 | Gagner et al. |
| 2012/0330330 A1 | 12/2012 | Gagner et al. |

OTHER PUBLICATIONS

International Search Report for International application No. PCT/US2011/020229, with a date of mailing of the international search report of Jun. 21, 2013, 6 pages.

METHODS AND APPARATUS FOR MAGNET-INDUCED COMPRESSION ANASTOMOSIS BETWEEN ADJACENT ORGANS

REFERENCE TO RELATED APPLICATIONS

This application is a continuation of U.S. application Ser. No. 12/984,803, filed Jan. 5, 2011, which claims priority to U.S. Provisional Application No. 61/292,313, filed Jan. 5, 2010, the contents of each of which are incorporated herein by reference in their entirety.

FIELD OF THE INVENTION

In general, the invention relates to surgical methods, apparatus and kits. More particularly, the invention relates to methods, apparatus and kits for magnet induced compression anastomosis.

BACKGROUND OF THE INVENTION

Current approaches to surgical treatments for gallbladder disease include open surgical resection, laparoscopic resection, and most recently natural orifice transluminal endoscopic surgery. The risks of these aforementioned techniques include the risks of trans-abdominal and/or transluminal incision (bleeding, infection, perforation, post-operative pain, adhesions, incisional hernia, risks of anesthesia).

Endoscopic approaches to treat gallbladder or biliary disease have been previously reported. Cholecystogastrostomy creation using endoscopic ultrasound assisted T-tag placement has been described. This technique requires breach of the gastric and gallbladder walls.

Another technique has utilized neodymium magnets for the creation of magnet compression anastomosis between the common bile duct and the small intestine. However, this treats obstruction of the common bile duct and does not address alternative gallbladder access, nor does it treat gallbladder disease per se.

A clinical need thus exists for a more minimally invasive procedure and enabling technology which will facilitate the creation of anastomosis between two adjacent organs in the gastrointestinal tract to create an opening between said organs as a replacement procedure for laparoscopic cholecystectomy and/or cholecystogastrostomy.

SUMMARY OF THE INVENTION

Aspects of the invention relate to materials, apparatus, methods, and kits for creating a fistula, anastomosis, or opening between two adjacent organs. In particular embodiments, the organs are adjacent gastrointestinal organs, such as, for example, the stomach and the gallbladder, the small intestine and the gallbladder, the stomach and the duodenum, or the ileum and the colon.

The present invention involves the use of a parent magnet and one or more daughter magnets. The parent magnet can be a permanent rare-earth disc or ring magnet (e.g., neodymium-boron-iron (NdBFe) or samarium-cobalt (SmCo), of the appropriate size and/or shape to fit within an endoscope, catheter, or other surgical instrument. Preferably, the parent magnet is a permanent magnet in the form of a disc with a diameter between 0.5 cm to 6 cm, e.g., 1 cm to 3 cm. The parent magnet can include a magnetic portion adapted to generate a magnetic field, and an attachment portion connected to the magnetic portion. In such embodiments, the attachment portion is preferably constructed and adapted to attach the parent magnet to a tissue. For example, the attachment portion can be an endoscopic clip or a suture.

The daughter magnets or magnetic materials are responsive to the magnetic field of the parent magnet so as to be attracted to the parent magnet through one or more tissues of varying degrees of thickness. The one or more daughter magnets or magnetic materials can include a plurality of ferromagnetic steel ball-bearings or discs. Alternatively, the daughter magnet(s) can be in the form of a magnetic slurry or paste. In a particular embodiment, the one or more daughter magnets are separate magnetic components that are adapted to self-assemble into a larger magnetic structure. The daughter magnet(s) or magnetic materials are appropriately sized and/or shaped for delivery into an organ through an endoscopic instrument and/or system, or a catheter, such as a biliary catheter.

Both the parent and daughter magnets may be made of a biocompatible material or coated with respective biocompatible coatings.

One aspect of the invention involves an apparatus for creating a fistula or an anastomosis between two adjacent organs, such as the stomach and the gallbladder, the small intestine and the gallbladder, stomach and the duodenum, or the ileum and the colon. The apparatus includes a parent magnet having a magnetic portion for generating a magnetic field and an attachment portion connected to the magnetic portion for attaching the parent magnet to a tissue, as described herein. The parent magnet is preferably appropriately sized and shaped, as described herein, for fitting within an endoscope or a catheter. The apparatus further includes one or more daughter magnets or magnetic materials, as described herein, that are responsive to the magnetic field generated by the parent magnet so as to be attracted to the parent magnet through one or more tissues of varying degrees of thickness.

Other aspects of the invention involve the use and placement of a parent magnet or magnetic assembly, as described herein, within a first organ, and the use and placement of one or more daughter magnets or magnetic materials, as described herein, within a second organ adjacent to the first organ. One aspect of the invention involves a method for creating a compression anastomosis between a gallbladder and an adjacent organ, such as the stomach or the small intestine, by placing a parent magnet within the adjacent organ such that it positioned against the proximate wall of the organ that is adjacent to the gallbladder, and introducing one or more daughter magnets or magnetic materials into the gallbladder such that the one or more daughter magnets are magnetically attracted to the parent magnet in the adjacent organ through a defined tissue area between the combined thickness of the two organ walls. The parent magnet may, for example, be introduced by an endoscope, while the daughter magnets or magnetic materials may be introduced into the gallbladder by a catheter, such as a biliary catheter. In alternate embodiments, the daughter magnets or magnetic materials are injected from an adjacent organ (e.g., the stomach or small intestine) into the gallbladder under the guidance of a visualization technology, such as endoscopic ultrasound. For example, endoscopic ultrasound may be used to inject the daughter magnets from the stomach (or the small intestine), through the combined thickness of the stomach wall (or intestinal wall) and the gallbladder wall, into the gallbladder, via the use of Endoscopic Ultrasound, Fine Needle Aspiration (EUS FNA) or other such techniques known to persons skilled in the art of diagnostic and therapeutic endoscopy. Once the parent and daughter magnets have been positioned within their respective organs, they are left in place for a defined amount of time, exerting compressive magnetic forces on the tissue walls, until the tissue necroses and an opening, anastomosis, or fistula is formed between the two adjacent organs.

Another aspect of the invention involves a method for at least partially inactivating a gallbladder by placing a parent magnet proximate to a wall of an adjacent organ proximate to the gallbladder (e.g., the stomach or the small intestine), introducing one or more daughter magnets or magnetic materials into the gallbladder such that the one or more daughter magnets are magnetically attracted to the parent magnet in the adjacent organ through a defined tissue area between the combined thickness of the two organ walls, allowing the tissue in the defined area to necrose to create an anastomosis between the gallbladder and the adjacent organ, removing the first magnet and one or more second magnets, then selectively inducing gallbladder scarring or damage through the anastomosis. The parent magnet may be introduced by an endoscope, while the daughter magnets or magnetic materials may be introduced into the gall bladder by a catheter, such as a biliary catheter, or injected from an adjacent organ (e.g., the stomach or small intestine) into the gallbladder via the use of Endoscopic Ultrasound, Fine Needle Aspiration (EUS FNA) or other such techniques known to persons skilled in the art of diagnostic and therapeutic endoscopy.

Kits according to embodiments of the invention may include, for example, a parent magnet as described herein and one or more daughter magnets or magnetic materials as described herein, the one or more daughter magnets or materials being preloaded into an introducing device such as a biliary catheter, or an endoscope such as an endoscopic ultrasound guided fine needle aspiration needle and/or system. Optionally, the kit(s) of the invention can include a grasping snare or pinchers.

Other aspects, features, and advantages of the invention will be set forth in the description that follows.

BRIEF DESCRIPTION OF THE DRAWINGS

The invention will be described with respect to the following drawing figures, in which.

DETAILED DESCRIPTION

The present invention is based on the discovery that an opening may be created in an organ wall or sheet of tissue using magnets. For example, a compression anastomosis or fistula may be created between adjacent abdominal/gastrointestinal organs, such as for example, the stomach and the gallbladder, the small intestine and the gallbladder, the stomach and the duodenum, or the ileum and the colon, using magnets. As used herein, the term "compression anastomosis" refers to the procedure of compressing together the walls of adjacent organs to induce a necrosis/healing process leading to the joining of the lumina of the two organs. The term "fistula" refers to an artificial or abnormal connection or passageway between two epithelium-lined organs that are not normally connected.

Figure 1:
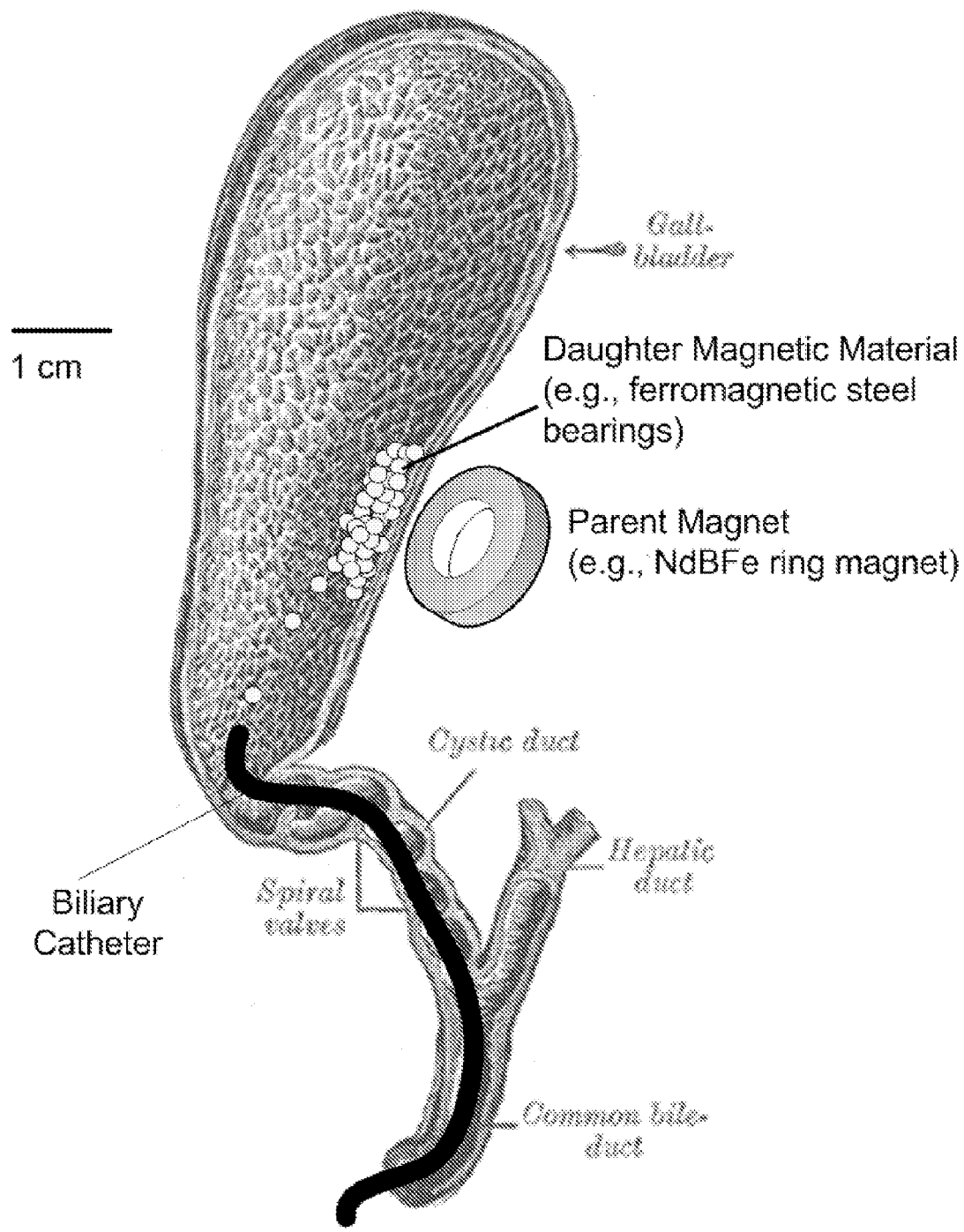
FIG. 1 is a schematic illustration of the gallbladder, generally illustrating the positioning of parent and daughter magnets to create a compression anastomosis, and particularly, the delivery of daughter magnetic material through a biliary catheter to the gallbladder.

FIG. 1 is a schematic illustration of the gallbladder, showing a parent magnet on one side of the organ wall and a daughter magnet, made of a paramagnetic or ferromagnetic material, on the other side of the organ wall. In the illustrated scenario, the parent magnet resides on or is secured to the stomach wall (not shown in FIG. 1). Once installed, the parent magnet and daughter magnet are left in place, with the magnetic attractive forces between them compressing the organ wall or walls, until an opening or anastomosis is created.

The parent magnet may, for example, comprise a permanent magnet such as a rare-earth disc or ring magnet (e.g., neodymium-boron-iron (NdBFe) or samarium-cobalt (SmCo) attached to a means of mucosal or tissue fixation, such as an endoscopic clip (Olympus QuickClip 2 Hemostatic Clip device, Olympus Corporation, Tokyo, Japan), via a connection, such as suture. In some embodiments, the parent magnet is large enough and of a shape appropriate to create an opening of a size and shape sufficient for an endoscope, catheter, or other surgical instrument to pass through. For example, in the embodiment of FIG. 1, the parent magnet is in the form of a disc with a diameter between 0.5 cm to 6 cm, but with a preferable diameter of 1 cm to 3 cm. This range of diametric sizes creates an anastomosis large enough to avoid stricture formation that may prohibit endoscopic access.

One advantage of systems, methods, and kits according to embodiments of the invention is that the parent magnet and the daughter magnet need not be of the same shape, size, or characteristics. For example, the parent magnet may be relatively larger and adapted for delivery using one type or size of instrument, while the daughter magnet or magnets may be of a different form and adapted for delivery using a different type of instrument.

The one or more daughter magnets or magnetic materials can include a plurality of paramagnetic or ferromagnetic steel ball-bearings or discs having a sufficient size and/or shape for delivery by syringe using air or water pressure through an endoscopic biliary catheter, or a fine needle aspiration needle. For example, The bearings or discs may small enough to be deployed endoluminally via the cystic duct or can be endoscopically injected directly into the gallbladder from an adjacent organ (e.g., the stomach) with the aid of endoscopic ultrasound (EUS) techniques, such as, for example, Endoscopic Ultrasound, Fine Needle Aspiration (EUS FNA). This technique differs from a conventional cholecystogastrostomy using T-tags because the fistula is created by means of magnetic anastomosis rather than endoscopic suturing. In an alternative embodiment, the one or more daughter magnets or magnetic materials can include a magnetic slurry or paste.

The parent and daughter magnets or magnetic materials would generally be made of a biocompatible material or coated with a biocompatible coating, such as Parylene (Specialty Coating Services (SCS), Indianapolis, Ind.) or other biocompatible coating materials, known to persons skilled in the art.

Figure 2:
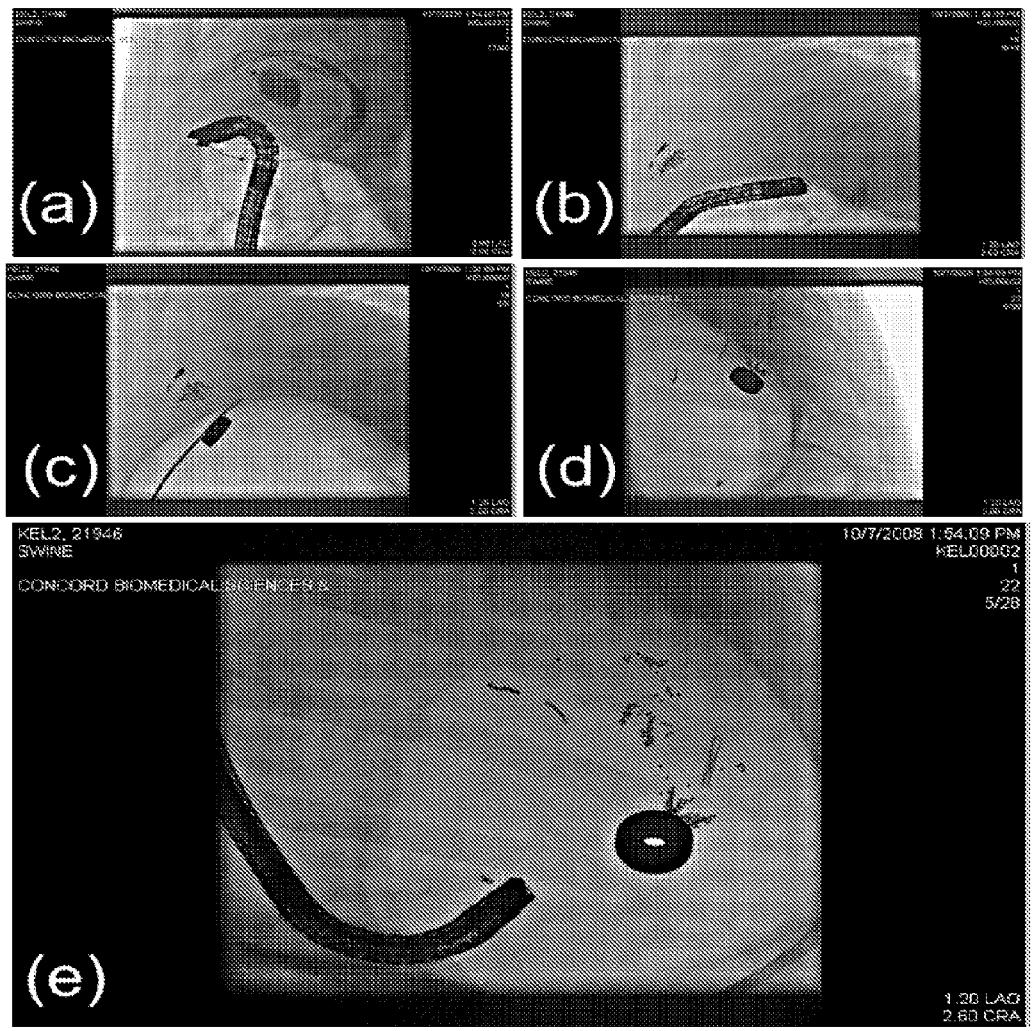
FIGS. 2A-2E are radiographic views illustrating the deployment and retrieval of parent and daughter magnets to create an anastomosis between the gallbladder and the stomach.

The drawings depicted in FIGS. 2A-2E are views illustrating by example, the deployment and retrieval of parent and daughter magnets to create an anastomosis between the gallbladder and the stomach. Specifically, FIGS. 2A and 2B show deployment of paramagnetic 52100 steel ball-bearings into the gallbladder via a biliary catheter. FIG. 2C shows deployment of a NdBFe parent magnet which is endoscopically clipped to the stomach wall. Capture of the bearings, shown in FIGS. 2D and 2E, by the parent magnet, results in apposition of the daughter and parent magnets for the anastomosis.

In another embodiment of the invention, the daughter magnet or magnetic material, which may be used as the intra-gallbladder component in a stomach-gallbladder anastomosis, comprises a second rare-earth magnet that can be delivered by syringe using air or water pressure through an endoscopic biliary catheter or endoscopically injected into the gallbladder from an adjacent organ (e.g., the stomach) with the aid of EUS FNA methodologies. Since the size of any one daughter element is limited by the cystic duct diameter, this embodiment may utilize a "self-assembling" structure for the magnetic elements, such that after deployment into the gallbladder, the daughter magnet's elements combine to form a larger structure, thus creating sufficient force between the parent and daughter magnets to result in anastomosis. This type of magnetic self-assembly is schematically illustrated in FIGS. 3A-3D, in which a train of daughter magnet components are injected into the gallbladder.

Figure 3:
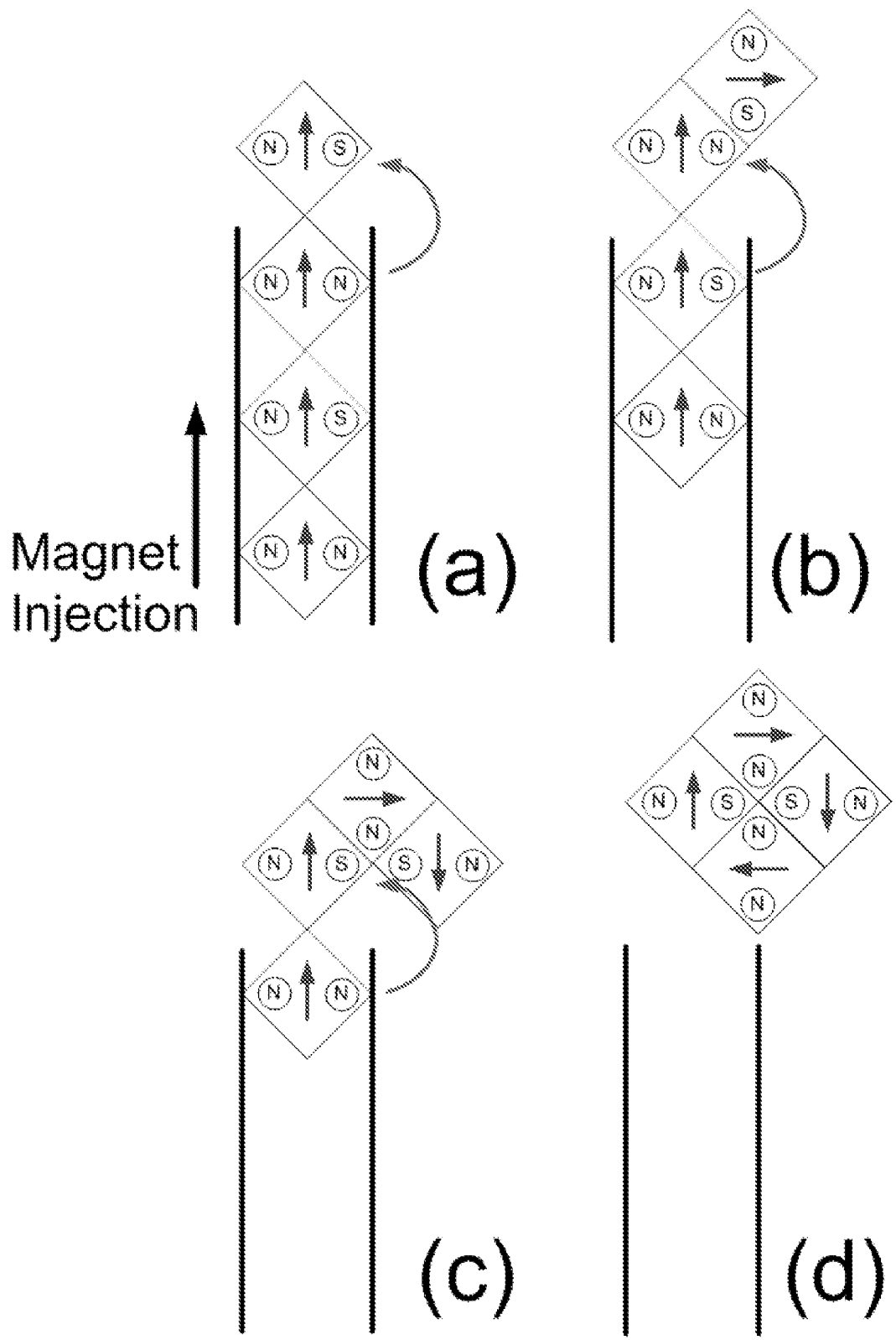
FIGS. 3A-3D are schematic views of a plurality of magnets in the lumen of a catheter, illustrating the process of magnetic self-assembly as the magnets are ejected from the catheter.

The components each carry two miniature magnets of variable magnetic polarity (e.g., north (N) or south (S)). In the case of quadrapolar magnets, three magnet component combinations are possible: (i) N-N, (ii) S-S and (iii) N-S (which is equivalent to S-N upon rotation by 180° for symmetric components). The daughter magnet components are small enough to fit through the inner diameter of the biliary catheter or EUS FNA device or FNA needle. Careful selection of the injection sequence can yield a larger planar surface upon self-assembly within the gallbladder than would be possible with any single component. The large daughter magnet in FIG. 3D is assembled by means of the following magnet component sequence (leftmost polarity first): N-S, NN, N-S, N-N. FIGS. 3A-3D represent the simplest example of magnetic self-assembly, and a much larger number of daughter magnet components can be used in practice to provide sufficient mating area with the parent magnet in the small intestine or stomach wall for effective anastomosis.

Figure 4:
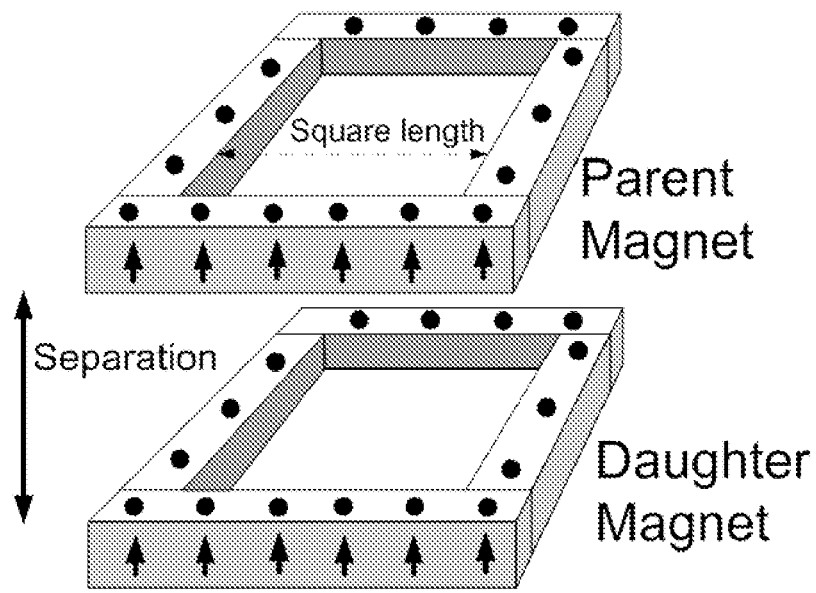
FIG. 4 depicts the arrangement for self alignment between assembled parent and daughter magnets using north/south attractive magnet forces.

The simplest embodiment of a self-assembling magnet results from a dipolar train of free (i.e. unconnected) rectangular or cylindrical magnets extruded into space where the direction of magnetic polarization is perpendicular to the direction of extrusion and the magnetization direction increases in consecutive components by 90° with each. For four rectangular components, where the direction of magnetization of consecutive components is 0°, 90°, 180° and 270° in the plane perpendicular to extrusion, the resultant assembly will be a four-sided rectangle (or a square in the case of identical components), as shown in FIG. 4. If this first magnetic train comprises the daughter magnet and a second, identical magnetic assembly comprises the parent magnet then mating occurs when the two opposing pole faces (i.e., north and south in the case of FIG. 4) come into proximity and the magnetic attractive forces between the two assemblies cause compressive attraction between the parent and daughter magnets. This compressive attraction which acts to compress the intervening gastric and gall bladder walls is theoretically sufficient to produce a leak-free magnetic anastomosis within a period of three to five days. The resultant window of access is accessed by means of needle-knife incision or similar endoscopic cautery, known to persons skilled in the art.

FIG. 4 shows the arrangement for self alignment between assembled parent and daughter magnets, using purely north/south attractive magnet mating. This configuration is suitable for generating significant compressive force sufficient for the creation of magnetic anastomosis using NdFeB magnetic components. However, to avoid repulsion between the parent and daughter assemblies, the opposing faces (i.e., north/south) need to be in closest contact.

Figure 5:
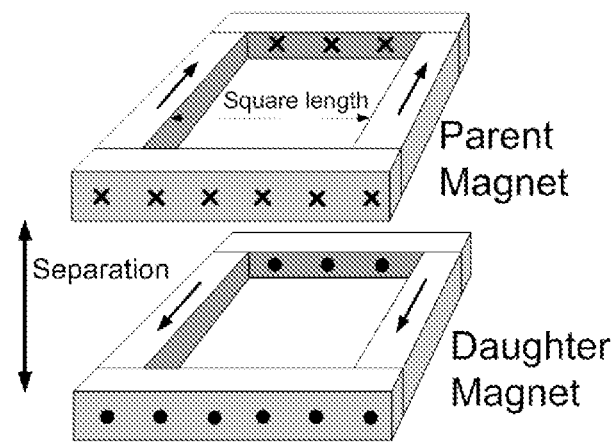
FIG. 5 depicts the arrangement for self alignment between assembled parent and daughter magnets, using "east/west" attractive magnetic forces.

FIG. 5 shows the arrangement for self alignment between assembled parent and daughter magnets, using what we term "east/west" attractive magnetic forces. This attraction takes advantage of the necessity for magnetic flux lines to form closed paths leading to a strong compressive force between the parent and daughter assemblies. While necessarily less than the compressive force for purely N/S attraction, this configuration may also be suitable for generating significant compressive force sufficient for the creation of magnetic anastomosis using NdFeB magnetic components when the separation distance is small (<1 mm) and high grade magnetic components (e.g., N50 or higher) are employed. The advantage of this configuration is that compression occurs independent of which faces are in contact and self alignment is again achieved.

Figure 6:
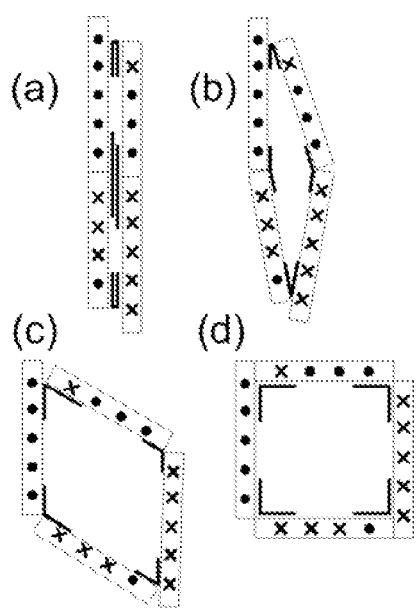
FIGS. 6A-6D illustrates the concept of "Magnet Self Assembly" in a connected train of magnetic components including a combination of quadruple and dipole components.

FIG. 6 illustrates the concept of "Magnet Self Assembly" in a connected train of magnetic components. When a combination of quadruple and dipole components are employed, a repulsive magnetic force can be used to ensure self assembly. As shown in FIG. 6, the self assembly is due to the repulsive forces associated with neighboring S poles (indicated by the solid circles) in the upper two components and the neighboring N poles (indicated by the crosses) in the lower two components which, together, drive the assembly into the final four-sided window.

In an alternate embodiment of the present invention, the intra-gallbladder daughter material may comprise a (super)

paramagnetic fluid consisting of iron-oxide particles or a suspension of iron filings. In the presence of the parent magnet, the (super)paramagnetic fluid would be strongly attracted to the parent magnet again, resulting in anastomosis due to the pressure between the two surfaces.

When external magnets are applied to the ferromagnetic daughter material they can be permanently magnetized to enhance the force of attraction between the parent magnet and the daughter material.

In the case of a stomach-gallbladder anastomosis, the parent magnet may be placed on the lumen of the small intestine or on the stomach wall using an endoscope that is introduced per-orally. The parent magnet may be fixed to the mucosa of the small intestine or stomach using an endoscopic clip.

One method for deploying the daughter magnet or magnetic material would involve using the standard Endoscopic Retrograde Cholangiopancreatography (ERCP) technique and fluoroscopy, in which a biliary catheter is introduced over a guidewire into the gallbladder. The ball-bearings or other daughter magnetic material would be delivered to the gallbladder through the biliary catheter using air pressure or liquid pressure provided by syringe. Alternatively, the daughter magnet or magnetic material may be deployed by direct injection from an adjacent organ into the gallbladder with the aid of EUS FNA type systems.

Figure 7:
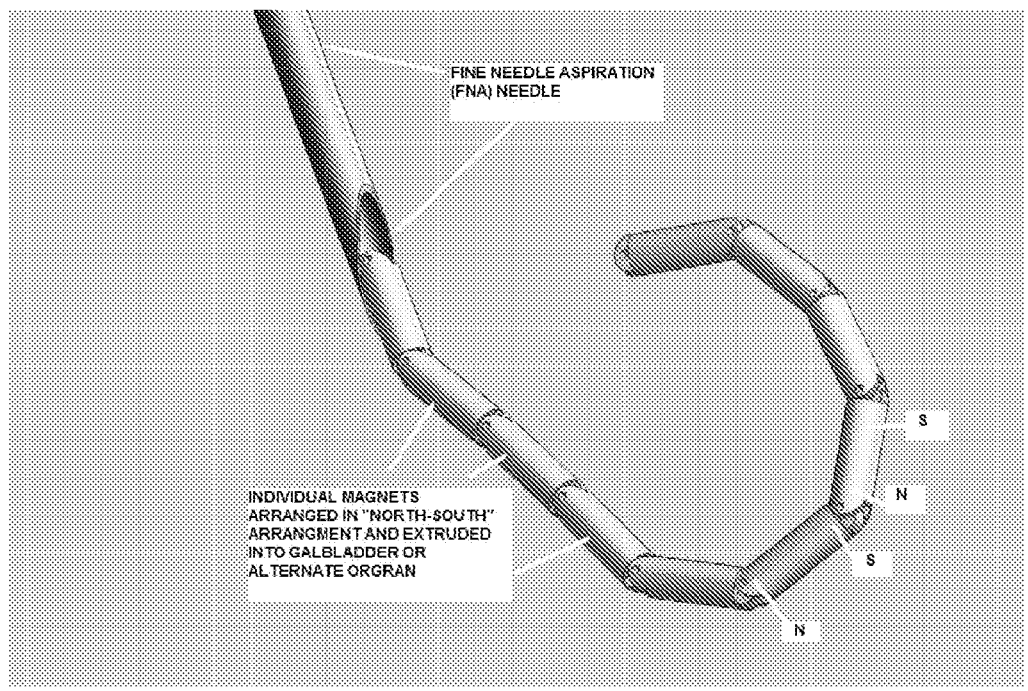
FIG. 7 depicts the extrusion of magnet components arranged in "North-South" arrangement from a fine needle aspiration (FNA) needle.
Figure 8:
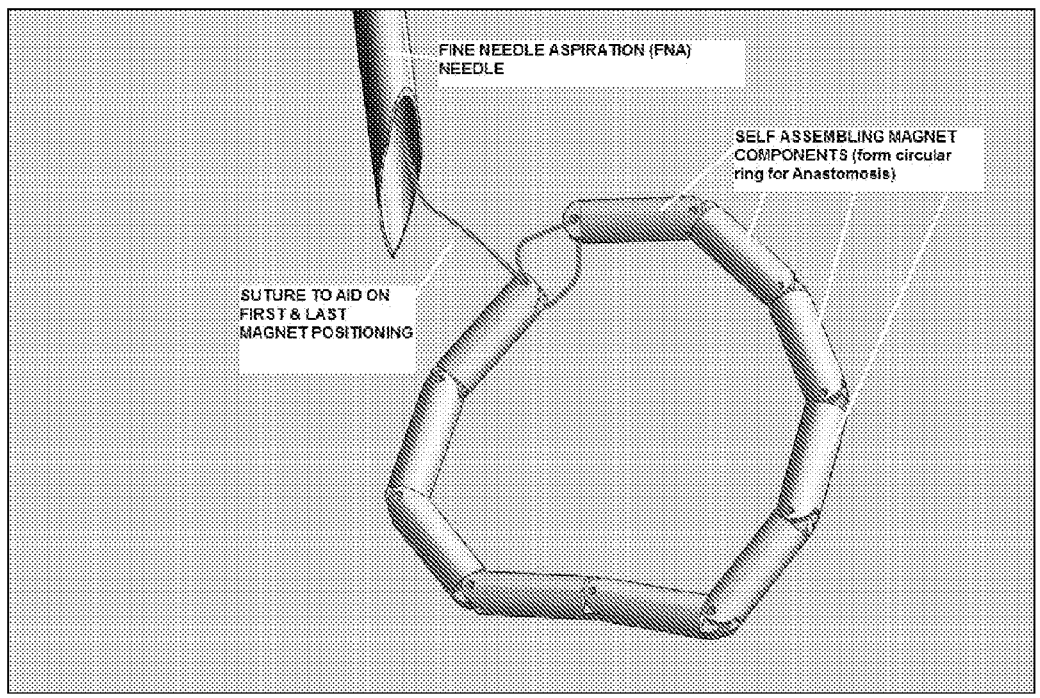
FIG. 8 depicts the self-assembly of the magnetic components depicted in FIG. 7 after extrusion from FNA needle and the use of a suture to connect the magnetic components.
Figure 9:
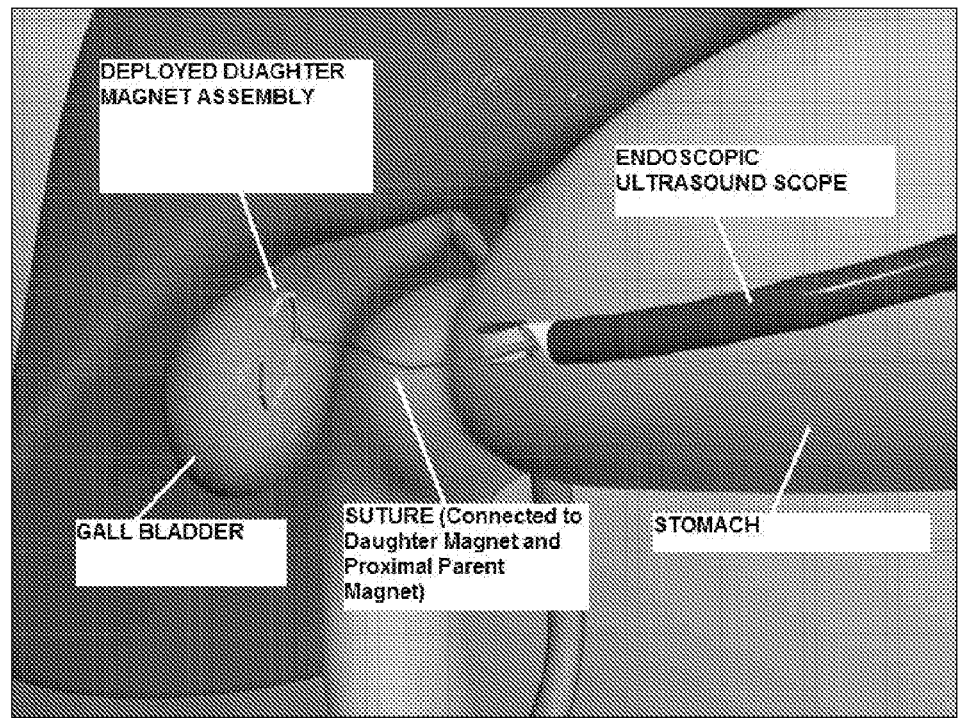
FIG. 9 depicts the deployment of daughter magnets from the stomach into the gallbladder using endoscopic ultrasound, the assembly of the daughter magnets in the gallbladder, and the positioning of a suture in the stomach upon retraction of the endoscopic ultrasound scope.
Figure 10:
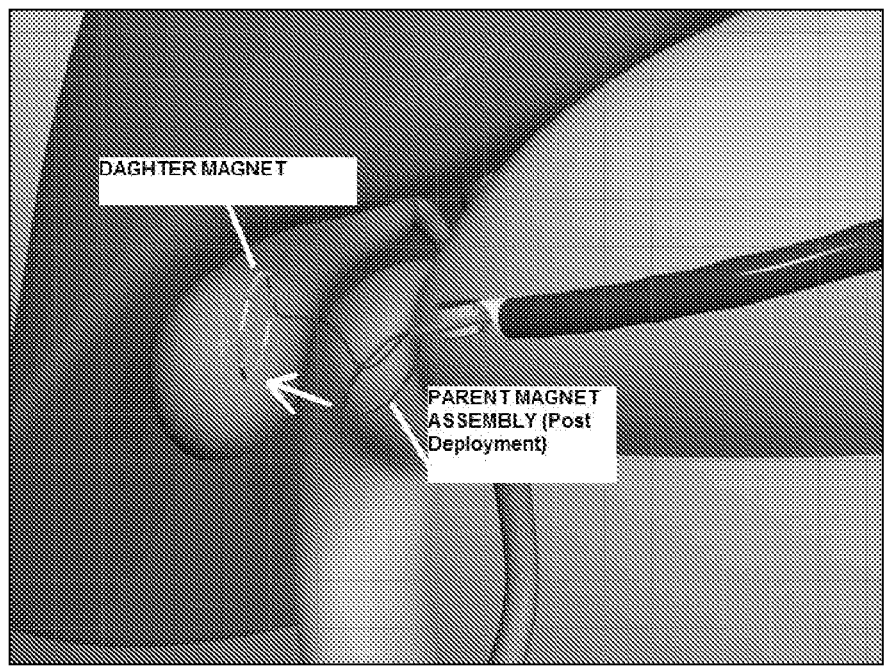
FIG. 10 depicts the assembly of daughter magnets in the gallbladder, the deployment and assembly of a parent magnet in the stomach, and the positioning of a suture connecting the daughter magnet assembly and the parent magnet assembly.
Figure 11:
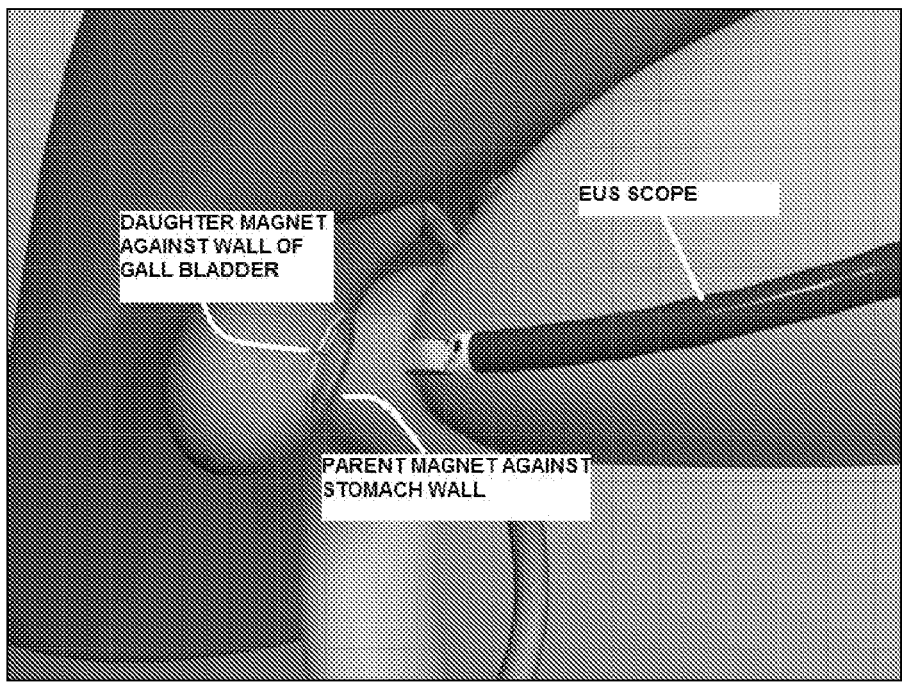
FIG. 11 depicts the magnetic attraction of daughter magnet assembly positioned against the wall of a gallbladder and a parent magnet positioned against an adjacent stomach wall.

As previously stated, the magnets may be delivered from one organ (e.g., the stomach) into another adjacent organ (e.g., the gallbladder) via a Fine Needle Aspiration (FNS) needle as illustrated in FIGS. 7 and 8. In this alternate embodiment, the individual magnets are circular in nature and pre-assembled in a N-S arrangement and injected through the inner lumen of the needle under endoscopic ultrasound guidance. These magnets may also be polarized in a N-S arrangement around the circumference of the magnet to provide for a means of apposition with the parent magnet once positioned. The distal and proximal magnets are pre-loaded with a suture through the distal and proximal eyelets of the distal and proximal magnet elements respectively. Once injected through the needle or biliary catheter, the distal and proximal magnet elements are secured together by tying off the pre-attached suture. As shown in FIG. 9, the suture is connected at the distal end to the deployed magnetic daughter assembly and runs antegrade through the inner lumen of the aspiration needle or biliary catheter. Once the needle is retracted through the wall of the stomach, the suture remains connected at the proximal end to the parent magnet assembly as shown in FIGS. 9 and 10. Once the parent magnet has been deployed into the stomach or other organ, both daughter and parent magnets are pushed together to great a tissue apposition between gallbladder and stomach as shown in FIG. 11.

Once deployed, magnet fixation is then achieved using EUS-guided T-tag delivery through the gallbladder wall with a second attachment to parent magnet in the stomach or small intestine, ensuring lock-in of parent magnet to the daughter. Such a T-tag procedure is well known to persons skilled in the art of therapeutic endoscopy. Using fluoroscopic guidance, magnetic attraction between the parent magnet and the intra-gallbladder ball-bearings can then be confirmed.

When the parent and daughter magnets are left in place for a period of time, the compressive forces on the tissue between the two magnets causes the tissue to necrose, leaving an opening surrounded by a fibrotic or collagenous border. After a period of several days (3-15), the creation of an opening, such as a cholecystogastrostomy, can be confirmed by upper endoscopy or another such technique. At that time, the cholecystogastrostomy can be traversed using the upper endoscope for the purpose of mucosal ablation. Mucosal ablation may be achieved using argon plasma coagulation (APC), electrocautery, laser, or instillation of sclerosant (e.g. alcohol or ethanolamine or sodium morrhuate). A prophylactic biliary stent may optionally be placed by endoscopic retrograde cholangiopancreatography (ERCP) prior to gallbladder mucosal ablation.

The purpose of gallbladder ablation is to induce scarring down of the gallbladder (i.e. functional cholecystectomy). This can be confirmed with a follow-up endoscopy or by radiographic (e.g. oral contrast study) or nuclear medicine study (e.g. biliary scintigraphy or HIDA study).

Aspects of the invention relate to a surgical kit or kits that contain all the additional, specialized surgical tools used to perform the tasks described above. For example, surgical kits of the invention at least include a parent magnet as described herein, and one or more daughter magnets as described herein, loaded into an introduction device such as a biliary catheter or an endoscopic instrument (e.g., EUS FNA needle and/or system). In one embodiment, the kit(s) of the invention include, but are not be limited to, (i) the parent magnet in a suitable biocompatible enclosure (e.g., Parylene or biocompatible plastic) and (ii) the daughter magnet material, preloaded for deployment. Optionally, the kit(s) of the invention include a grasping snare or pinchers for assisting with the introduction and placement of the parent and/or daughter magnets.

For embodiments or situations in which the daughter magnet or magnetic material is injected directly into the gallbladder (either by transgastric means or via the small intestine wall), the daughter magnetic material may be preloaded in an EUS FNA injection needle with an outer diameter in the range of 10 Gauge to 25 Gauge, but more preferably in the range of 15 Gauge to 20 Gauge. Deployment of both magnets into the gallbladder and/or stomach can be achieved with the aid of EUS FNA is this instance.

It should be noted that the present invention is not limited to the clinical applications listed in the afore-described disclosure. The technology as per the disclosed description may also be utilized to achieve an anastomosis between other adjacent organs in both the upper and lower gastrointestinal tracts such as, but not limited to, between the small intestine/gallbladder, the stomach/duodenum and the ileum/colon for bariatric/metabolic purposes. The daughter and parent magnet components may be delivered during simultaneous endoscopy and colonoscopy procedures and mated under fluoroscopy. The afore-mentioned endoscopy and colonoscopy procedures are well known to persons skilled in the art of therapeutic endoscopy.

While the invention has been described with respect to certain embodiments, the embodiments are intended to be exemplary, rather than limiting. Modifications and changes may be made within the scope of the appended claims.

What is claimed is:

1. An implantable device for creating an anastomosis, the device comprising:
    an assembly of magnetic segments associated with one another, each of the magnetic segments having opposing poles and directly joined to an immediately adjacent magnetic segment at one of the opposing poles, the assembly configured to transition between a delivery configuration and a deployed configuration;

wherein, when in the delivery configuration, the magnetic segments are aligned end-to-end in a single-file arrangement and the assembly is substantially linear; and wherein, when in the deployed configuration, the magnetic segments self-assemble into a geometric shape based, at least in part, on an attractive force between immediately adjacent magnetic segments.

2. The implantable device of claim 1, wherein at least one of the magnetic segments is directly joined to an immediately adjacent magnetic segment by way of a mechanical connection.

3. The implantable device of claim 1, wherein at least one of the magnetic segments is directly joined to an immediately adjacent magnetic segment by way of an attractive magnetic force.

4. The implantable device of claim 3, wherein each magnetic segment has an N pole facing a first direction and an S pole facing an opposing second direction, such that the N pole is proximate to an S pole of an immediately adjacent magnetic segment.

5. The implantable device of claim 1, wherein the geometric shape is angular, polygonal, annular, or spiral.

6. The implantable device of claim 1, wherein, when in the deployed configuration, a most-distal magnetic segment of the delivery configuration and a most-proximal magnetic segment of the delivery configuration are directly joined to one another.

7. The implantable device of claim 1, wherein, when in the delivery configuration, the assembly of magnetic segments is sized to fit within an introducing device for introduction into and implantation within a first organ.

8. The implantable device of claim 7, wherein the assembly of magnetic segments is configured to respond to a magnetic field generated by a separate associated magnetic assembly implanted within a second organ such that both magnetic assemblies are magnetically attracted to one another through a defined tissue area of the combined thickness of walls of the two organs and exert compressive forces on the defined area.

9. The implantable device of claim 8, wherein the two organs are selected from the group consisting of the gallbladder, the stomach, the small intestine, and the large intestine.

10. The implantable device of claim 7, wherein the introducing device is selected from the group consisting of an endoscope, a trocar, a cannula, a catheter, and a fine needle aspiration device.

11. An implantable device for creating an anastomosis, the device comprising:
an assembly of elongated magnetic segments associated with one another and configured to transition from a compressed delivery configuration, wherein at least two adjacent elongated magnetic segments are substantially parallel and in close proximity with one another, to an expanded deployed configuration, wherein the elongated magnetic segments are configured to self-assemble into a geometric structure based, at least in part, on a repulsive magnetic force between corresponding portions of the at least two adjacent elongated magnetic segments, such that the at least two adjacent elongated magnetic segments are substantially perpendicular to one another in the expanded deployed configuration.

12. The implantable device of claim 11, wherein the at least two adjacent elongated magnetic segments are connected with a hinge element.

13. The implantable device of claim 12, wherein ends of the at least two adjacent elongated magnetic segments proximate to the hinge exert attractive magnetic force on each other and corresponding opposing ends of the at least two adjacent elongated magnetic segments exert repulsive magnetic force on each other.

14. The implantable device of claim 13, wherein one of the at least two adjacent elongated magnetic segments comprises an N pole at one end and an S pole at the opposing end and the other of the at least two adjacent elongated magnetic segments comprises an S pole at both ends or an N pole at both ends.

15. The implantable device of claim 11, wherein the device comprises four or more elongated magnetic segments configured to self-assemble into a polygon.

16. The implantable device of claim 15, wherein the polygon is a rectangle.

17. The implantable device of claim 11, wherein, when in the compressed delivery configuration, the elongated magnetic segments are sized to fit within an introducing device for introduction into and implantation within a first organ.

18. The implantable device of claim 17, wherein the geometric structure of the elongated magnetic segments is configured to respond to a magnetic field generated by separate associated magnetic assembly implanted within a second organ such that the geometric structure of elongated magnetic segments and the separate magnetic assembly are magnetically attracted to one another through a defined tissue area of the combined thickness of walls of the two organs and exert compressive forces on the defined area.

19. The implantable device of claim 18, wherein the two organs are selected from the group consisting of the gallbladder, the stomach, the small intestine, and the large intestine.

20. The implantable device of claim 17, wherein the introducing device is selected from the group consisting of an endoscope, a trocar, a cannula, a catheter, and a fine needle aspiration device.

* * * * *